(12) United States Patent
Ho et al.

(10) Patent No.: US 7,513,255 B2
(45) Date of Patent: Apr. 7, 2009

(54) PATIENT INTERFACE DEVICE WITH UNIVERSAL HEADGEAR MOUNTING MEMBER

(75) Inventors: Peter Chi Fai Ho, Pittsburgh, PA (US); Lance Busch, Trafford, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/440,628

(22) Filed: May 25, 2006

(65) Prior Publication Data

US 2006/0272646 A1    Dec. 7, 2006

Related U.S. Application Data

(60) Provisional application No. 60/687,644, filed on Jun. 3, 2005.

(51) Int. Cl.
*A62B 18/08* (2006.01)

(52) U.S. Cl. .............................. 128/207.11; 128/206.24; 128/206.27

(58) Field of Classification Search ............ 128/206.27, 128/206.24, 207.11, 207.17, 202.27, 206.21, 128/206.26, 206.28, 207.13
See application file for complete search history.

(56) References Cited

U.S. PATENT DOCUMENTS

| | | | |
|---|---|---|---|
| 5,662,101 A | 9/1997 | Ogden et al. | |
| D412,745 S | 8/1999 | Scheu | |
| 6,068,649 A * | 5/2000 | Chamberlain | 606/234 |
| 6,412,488 B1 | 7/2002 | Barnett et al. | |
| 6,463,638 B1 * | 10/2002 | Pontaoe | 24/614 |
| 6,467,483 B1 | 10/2002 | Kopacko et al. | |
| 6,516,802 B2 | 2/2003 | Hansen et al. | |
| 6,631,718 B1 | 10/2003 | Lovell | |
| 6,701,926 B2 * | 3/2004 | Olsen et al. | 128/207.11 |
| 6,823,869 B2 | 11/2004 | Raje et al. | |
| 6,851,425 B2 | 2/2005 | Jaffre et al. | |
| 6,860,268 B2 * | 3/2005 | Bohn et al. | 128/206.21 |
| 7,047,972 B2 * | 5/2006 | Ging et al. | 128/207.11 |
| 2002/0023649 A1 * | 2/2002 | Gunaratnam et al. | 128/205.25 |
| 2002/0148472 A1 * | 10/2002 | Barnett et al. | 128/206.24 |
| 2004/0025883 A1 | 2/2004 | Eaton et al. | |

(Continued)

FOREIGN PATENT DOCUMENTS

WO    WO 2004/014454    2/2004

(Continued)

OTHER PUBLICATIONS

Sleepnet Corporation, "Nasal masks for the treatment of Obstructive Sleep Apnea", 2003.

(Continued)

*Primary Examiner*—Justine R Yu
*Assistant Examiner*—Kristen C Matter
(74) *Attorney, Agent, or Firm*—Michael W. Haas

(57) ABSTRACT

A patient interface device of the invention includes a shell having a wall with a port extending therethrough, a conduit coupling in fluid communication with the port, and a mounting member rotatably. The mounting member is coupled to the conduit coupling, or both such that the mounting member is rotatable over a 360 degree range while the patient interface device is donned on a user and without locking in a fixed position relative to the shell or conduit while the patient interface device is donned on a user.

20 Claims, 12 Drawing Sheets

U.S. PATENT DOCUMENTS

2004/0045551 A1    3/2004   Eaton et al.
2005/0150497 A1*   7/2005   Eifler et al. ............ 128/206.21
2006/0130844 A1*   6/2006   Ho et al. ................ 128/206.24
2006/0144405 A1*   7/2006   Gunaratnam et al. ... 128/206.21

FOREIGN PATENT DOCUMENTS

WO    WO 2004/021960    3/2004

OTHER PUBLICATIONS

Sleepnet Corporation, "IQ Nasal Mask", Nov. 2003, www.sleep-net.com/iq.htm.

* cited by examiner

PATIENT INTERFACE DEVICE WITH UNIVERSAL HEADGEAR MOUNTING MEMBER

CROSS-REFERENCE TO RELATED APPLICATIONS

This application claims priority under 35 U.S.C. § 119(e) from provisional U.S. patent application Ser. No. 60/687,644, filed Jun. 3, 2005, the contents of which are incorporated herein by reference.

BACKGROUND OF THE INVENTION

1. Field of the Invention

The present invention pertains to a patient interface device, and, in particular, to a patient interface device that includes a mask and a mounting member that is coupled to and freely rotatable relative to the mask and that provides a connection of a headgear assembly. The free rotation of the mounting member and its configuration enables various configurations of headgear assemblies to be used with the same patient interface device, thereby providing convenience, ease-of-use, ease-of-adjustment and improved comfort to the patient.

2. Description of the Related Art

It is well known to treat a medical disorder or to diagnose, treat or monitor the condition of the patient, using medical equipment. For example, a patient may be monitored and treated for various sleep disorders in a sleep lab, home, or in some other setting. An example of a type of sleep disorder is obstructive sleep apnea, which is characterized by a collapse of the upper airways during sleep. Another sleep disorder is central sleep apnea, which is characterized by the suspension of all respiratory movement. Obstructive sleep apnea and central sleep apnea may also be combined in a condition referred to as mixed apnea.

In order to diagnose and/or treat such medical disorders, various equipment and devices are required for successful diagnosis and a resulting prescribed treatment. Further, there are numerous situations where it is necessary or desirable to deliver a flow of breathing gas, non-invasively, to the airway of a patient, i.e., without intubating the patient or surgically inserting a tracheotomy tube in their trachea. For example, it is known to ventilate a patient using a technique known as non-invasive ventilation. It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), congestive heart failure, stroke, Cheynes-Stokes respiration, etc. Non-invasive ventilation and pressure support therapies involve the placement of a patient interface device, which is typically a nasal or nasal/oral mask, on the face of a patient to interface the ventilator or pressure support device with the airway of the patient, so that a flow of breathing gas can be delivered from the pressure/flow generating device to the airway of the patient.

Patients suffering from a pulmonary or respiratory disorder, such as obstructive sleep apnea, are often treated with a pressure support device, such as a continuous positive airway pressure (CPAP) device. A CPAP device delivers a flow of fluid to the airway of the patient throughout the patient's breathing cycle in order to "splint" the airway, thereby preventing its collapse during sleep. In another type of treatment, bi-level positive pressure therapy is provided to the patient, in which the pressure of air delivered to the patient's airway varies or is synchronized with the patient's breathing cycle to maximize therapeutic effect and comfort to the patient. A pressure support device may also provide "bi-level" pressure support, in which a lower pressure is delivered to that patient during the patient's expiratory phase then during the inspiratory phase.

It is also known to provide an auto-titration positive pressure therapy in which the pressure provided to the patient changes based upon the detected conditions of the patient, such as whether the patient is snoring or experiencing an apnea, hypopnea, or upper airway resistance. Such a device adjusts the pressure delivered to the patient, based on whether or not the patient is snoring. For example, a pressure support device may actively test the patient's airway to determine whether obstruction, complete or partial, could occur and adjust the pressure output to avoid this result.

Other modes of providing positive pressure support to a patient are known. For example, a proportional assist ventilation (PAV®) mode of pressure support provides a positive pressure therapy in which the pressure of gas delivered to the patient varies with the patient's breathing effort to increase the comfort of the patient. Proportional positive airway pressure (PPAP) devices deliver breathing gas to the patient based on the flow generated by the patient.

For purposes of the present invention, the phrase "pressure support system", "pressure support device", or "positive pressure support" includes any medical device or method that delivers a flow of breathing gas to the airway of a patient, including, but not limited to, a ventilator, CPAP, bi-level, PAV, PPAP, or bi-level pressure support system.

Because such patient interface devices are typically worn for an extended period of time, a variety of concerns must be taken into consideration. For example, in providing CPAP or other positive pressure therapy to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy.

In order to provide a flow of gas to a patient, the patient must use a patient interface device, such as a respiratory mask, as known in the art to communicate the flow of gas with their airway. These respiratory masks are provided in many variations, such as nasal masks, nasal and oral masks, mouth masks, full-face masks, etc. However, all of these mask devices are used to provide a breathing gas, such as oxygen, air or a combination thereof, to the patient.

Typically, the flow of gas is provided by a pressure generating device, such as those devices discussed above, and is communicated from the pressure generating device to the patient interface device via a flexible conduit, which is also known as a patient circuit. It is also known to deliver the flow of gas from an oxygen source, such as a pressurized oxygen tank via a pressure regulator and a hose, to the patient interface device.

Typically patient interface devices include a mask shell having a cushion or seal member attached to the shell that contacts the surface of the patient. The mask shell and cushion are held in place by a headgear assembly that wraps around the head of the patient and is secured to the patient interface device. The mask and headgear in combination with the patient interface device form a patient interface device. A typical headgear assembly includes a headgear having flexible, adjustable straps that extend from the mask (patient interface device) to attach the mask to the patient. Other techniques for attaching a patient interface device use a vice-like device that anchors at the front and back of the patient's head to support the mask on the user. See, e.g., U.S. Pat. No. 6,516,802. While such conventional interface devices are generally accepted, there remains a class of users that do not find these devices to be sufficiently comfortable, too bulky, or otherwise inadequate. Thus, alternative techniques for interfacing a pressure support system to the airway of a patient are desired.

Because patient interface devices are typically worn for an extended period of time, it is important that the headgear assembly maintain the patient interface device in a tight enough seal against a patient's face to minimize gas leakage at the seal/patient interface without discomfort. Adjustability of the mask and/or the headgear, together with increased patient comfort, is paramount as is the maintenance of the seal between the mask and the user's face. According to the prior art, various headgear have been developed that position the straps in various locations with respect to the mask in order to effect this seal.

An example of a conventional patient interface device that includes a collar and mask assembly that allow for the variable positioning of headgear straps is described in U.S. Pat. No. 6,412,488 to Barnett et al. ("the '488 patent"). As best seen in FIGS. 4A and 4B of the '488 patent, in order to prevent rotational movement of the seal member relative to the collar, a mounting member on the collar includes multiple protrusions, and the neck portion of the seal includes matching channels for receiving these protrusions. Accordingly, when the seal member is attached to the collar, the protrusions and channels prevent the collar from rotating relative to the seal member. In addition, the protrusions and channels are arranged such that only proper alignment of the seal member relative to the collar is allowed. In one embodiment, a conduit coupling member, which couples the mask to the patient circuit, is rotatable about the collar. This allows for movement of the patient with respect to the patient circuit. However, the device of the '488 patent, while moveable between various positions, is not fully flexible or rotatable with respect to the mask to which it is attached.

Another collar device for attachment to a mask, and to allow variable positioning, is disclosed in U.S. Pat. No. 5,662,101 to Ogden et al. ("the '101 patent") The device taught by the '101 patent includes a rigid plate connected to a facial mask assembly by connecting detents on the plate to channels on the mask assembly. Straps are inserted through openings on the rigid plate in order to secure the mask assembly in a sealed position against the user's face. Multiple openings are available, such that a variety of strapping positions can be obtained. However, the assembly of the '101 patent is not rotatable with respect to the mask to which it is attached. A similar unrotatable plate or collar arrangement is illustrated in U.S. Design Pat. No. Des. 412,745 to Scheu.

Yet another conventional patient interface device that includes a collar is shown and described in U.S. Pat. No. 6,631,718 to Lovell ("the '718 patent"), which embodies a similar design and operation to the device taught by the '488 patent device. In particular, the Lovell device includes a retainer that is attachable to the shell of the mask. This retainer includes lower connection points and at least one upper connection point, as best illustrated in FIGS. 1, 2A, 7 and 9-11 of the '718 patent. While, like the device of the '488 patent, the assembly of the '718 patent permits multiple attachment points for variations in strap connection and positioning, the retainer is not rotatable about the shell of the mask. Instead, the retainer is positioned in a fixed position using tabs on the inlet of the mask and associated and mating slots on the retainer. Accordingly, while providing some variability in headgear or strap connection, the device disclosed in the '718 patent does not provide flexibility in attaching the headgear to the mask. A similar non-rotatable and inflexible headgear/strap assembly is disclosed in U.S. Pat. No. 6,823,869 to Raje et al., such as in, e.g., FIGS. A11 and F36.

SUMMARY OF THE INVENTION

Accordingly, it is an object of the present invention to provide a patient interface device that addresses the above-identified concerns and overcomes the shortcomings of conventional patient interface devices. This object is achieved according to one embodiment of the present invention by providing a patient interface device that includes a shell having a wall with a port extending therethrough. A conduit coupling is in fluid communication with the port. A mounting member, including a strap connection portion, is rotatably coupled to the shell, the conduit coupling, or both such that the mounting member is rotatable over a 360 degree range while the patient interface device is donned on a user and without locking the mounting member in a fixed position relative to the shell or conduit also while the patient interface device is donned on a user.

It is yet another object of the present invention to provide a method of attaching a patient interface device to a user that does not suffer from the disadvantages associated with conventional techniques. This object is achieved by providing a method that includes (a) providing a patient interface device comprising: (1) a shell having a wall with a port extending therethrough, (2) a seal member coupled to the shell and adapted to contact a surface of a user, (3) a conduit coupling in fluid communication with the port; and (4) a mounting member. The mounting member includes (i) a longitudinal axis, (ii) a first strap connection portion, and (iii) a second strap connection portion. The first strap connection portion and the second strap connection portion are disposed at generally opposites ends of the mounting member along the longitudinal axis. The method further includes (b) positioning the patient interface device on a user such that the seal member contacts a surface of such a user; (c) rotating the mounting member such that the longitudinal axis is generally perpendicular or is generally parallel to a longitudinal axis of such a patient; and (d) securing the patient interface device on the user using a headgear responsive to a selection of an orientation of the mounting member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
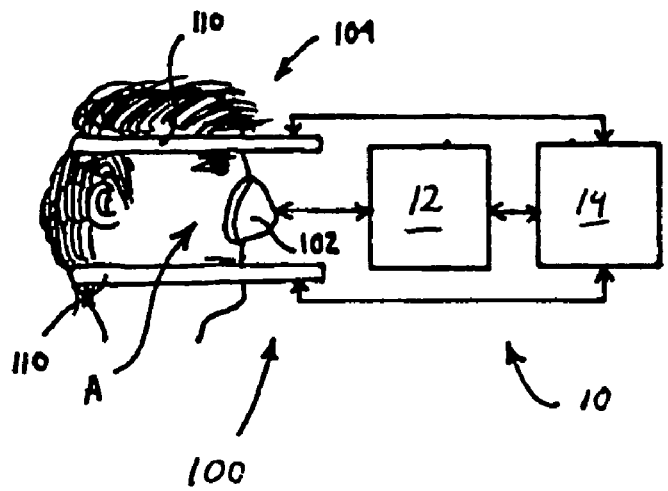
FIG. 1 is a schematic view of a patient interface device according to the principles of the present invention.

The present invention is directed to a patient interface device 100 that communicates a flow of gas to an airway of a patient. The patient interface device is illustrated in various embodiments in FIGS. 1-13, and is illustrated donned on a user's face A in FIGS. 10-12. The present invention is further directed to a patient interface device that is used in conjunction with a headgear assembly 104. The patient interface device includes a mask 102 and a mounting member 10 that couples a portion of a headgear assembly to the mask.

Headgear assembly 104 includes at least one, and typically multiple straps 110 for retaining patient interface device 100 in a sealed position with respect to the user's face A. One unique advantage of mounting member 10 of the present invention, as discussed in detail hereinafter, is that it is useful in connection with many different types and variations of headgear assemblies, and, in particular, headgear assemblies with different numbers of straps. For example, mounting member 10 can be used in connection with a three-point attachment assembly, a four-point attachment assembly, a vertically oriented attachment assembly, or a horizontally oriented attachment assembly. Any of these assemblies may include a number of straps 110 for securing the patient interface device against the user's face. As is known in the art, the length of the straps can be adjustable to control the strapping force that urges the patient interface device on the user's face.

With respect to the present invention, and as seen in schematic form in FIG. 1, mounting member 10 includes a strap connection portion 12 that connects to the straps of the headgear assembly. Further, strap connection portion 12 includes one or more strap attachment assemblies 14 for engaging at least one, and typically multiple, straps 110 of the headgear assembly. Still further, mounting member 10 is continuously rotatable with respect to mask 102 while one or more of straps 110 of mask attachment assembly 104 is engaged with strap attachment assembly 14 as indicated by Arrow B in FIG. 4. Thus, mounting member 10 is rotatable relative to the mask even after already having been attached to the mask, as well as after the straps of the headgear assembly are engaged therewith.

Referring now to FIGS. 1-6, patient interface device 100 includes mask 102 having a mask wall 108 with a mask port 106 extending therethrough. Such an arrangement is known in the art. The mask port allows for further attachment to other assemblies, such a elbow couples, conduits, etc., in order to provide gas into the mask for inhalation by the patient or user. In particular, mask 102 serves to provide a user or patient with gas, such as oxygen, air, room air, a combination of a gas and a medicine, etc., and this gas flows through mask port 106 and into the mask for inhalation.

In one embodiment, patient interface device 100 includes a conduit coupling 112 in fluid communication with mask port 106. As seen in FIGS. 2-6, conduit coupling 112 is connected to mask 102 and allows for a sealed transfer of gas through the conduit coupling, further through mask port 106 and into mask 102. In an exemplary embodiment of the present invention, conduit coupling 112 is rotatable relative to the mask as indicated by arrow C in FIG. 4.

The present invention also contemplates that conduit coupling 112 includes an exhaust port 114 for permitting the exhausted breath of the patient to flow from the mask, through the mask port, further through the conduit coupling and out of the exhaust port to the ambient atmosphere. The present invention contemplates that the exhaust port can have any configuration suitable for communicating exhaust gas to ambient atmosphere. One example of such an exhaust port 114 is shown and described in U.S. Pat. No. 6,851,425 to Jaffre et al.

As set forth above, patient interface device 100 includes headgear assembly 104 having multiple straps 110 for retaining the mask in a sealed position on the user's face A. Also as discussed above, the headgear assembly may be in the form of a headpiece wearable by the patient and having multiple and adjustable straps 110 attached thereto that extend around at least a portion of the user's head and attached to the patient interface device on the user's face. Mounting member 10 of patient interface device 100 includes strap connection portion 12 having strap attachment assembly 14 for engaging with the straps of the mask attachment assembly.

It is envisioned that mounting member 10 can be used in connection with and retrofitted on a previously-existing mask. Alternatively, the patient can be supplied with an assembled patient interface device according to the present invention. In either case, mounting member 10 provides a continuously rotatable, and therefore highly flexible, positioning and retainment system for the straps of the headgear assembly.

In operation, the user selects any number of different headgear assemblies 104 for use in connection with the patient interface device, because the configuration and coupling of the mounting member to the mask allows for different types or configurations of headgear assemblies to be used with a common patient interface device. This is quite different from conventional patient interface devices that are limited to a single type headgear assembly particularly suited for a specific type of mask. The present invention also provides the user with flexibility of movement, such as when sleeping or exercising, by allowing mounting member 10 to rotate freely over a range of 360 degrees relative to the mask, as indicated by arrow B. These features of the present invention permit the use of different headgear assemblies and/or movement of the user while the patient interface device is in use. Therefore, the user can use mounting member 10 of the present invention in connection with his or her preferred headgear assembly 104, without the requirement of obtaining an entirely different patient interface device 100 from the manufacturer.

Also, after the mask is attached to the user via the mask attachment assembly, and when using the mounting member of the present invention, even when the user is moving his or her head in various directions, the strap connection member, and therefore the strap attachment assembly, is capable of moving and rotating to prevent overly tight straps, which leads to discomfort, or strap disengagement, which will break the seal between the mask and the user's face A. Therefore, mounting member 10 of the present invention provides many unique and novel benefits with respect to the prior art patient interface devices and attachment assemblies.

In one embodiment, strap connection portion 12 of mounting member 10 includes at least one slot 16 extending through the mounting member. Specifically, slot 16 includes a bearing surface 20 for contacting and engaging one or more of straps 110 of headgear assembly 104. As seen in many of the embodiments illustrated in the figures, multiple slots 16 may be used, and these slots extend along the strap connection portion of the mounting member in order to provide multiple strap placement positions and variability.

In one embodiment, and as best seen in FIGS. 3-6, slot 16 includes at least one, and typically multiple, ridges 22 extending from an edge 24 of slot 16. In this manner, a single slot is separated into multiple and discrete recesses 26, and each of these recesses include a bearing surface for contacting and engaging a strap of the headgear assembly. The present invention also contemplates providing multiple discrete, i.e., separate, slots 16 in strap connection portion 12 of the mounting member. In one embodiment, each slot 16 extends substantially adjacent a periphery portion of the strap connection portion of the mounting member. Still further, the recesses of slot 16 in this embodiment are disposed in an end-to-end configuration along the periphery of the mounting member to provide maximum flexibility and variability in strap engagement.

Figure 7:
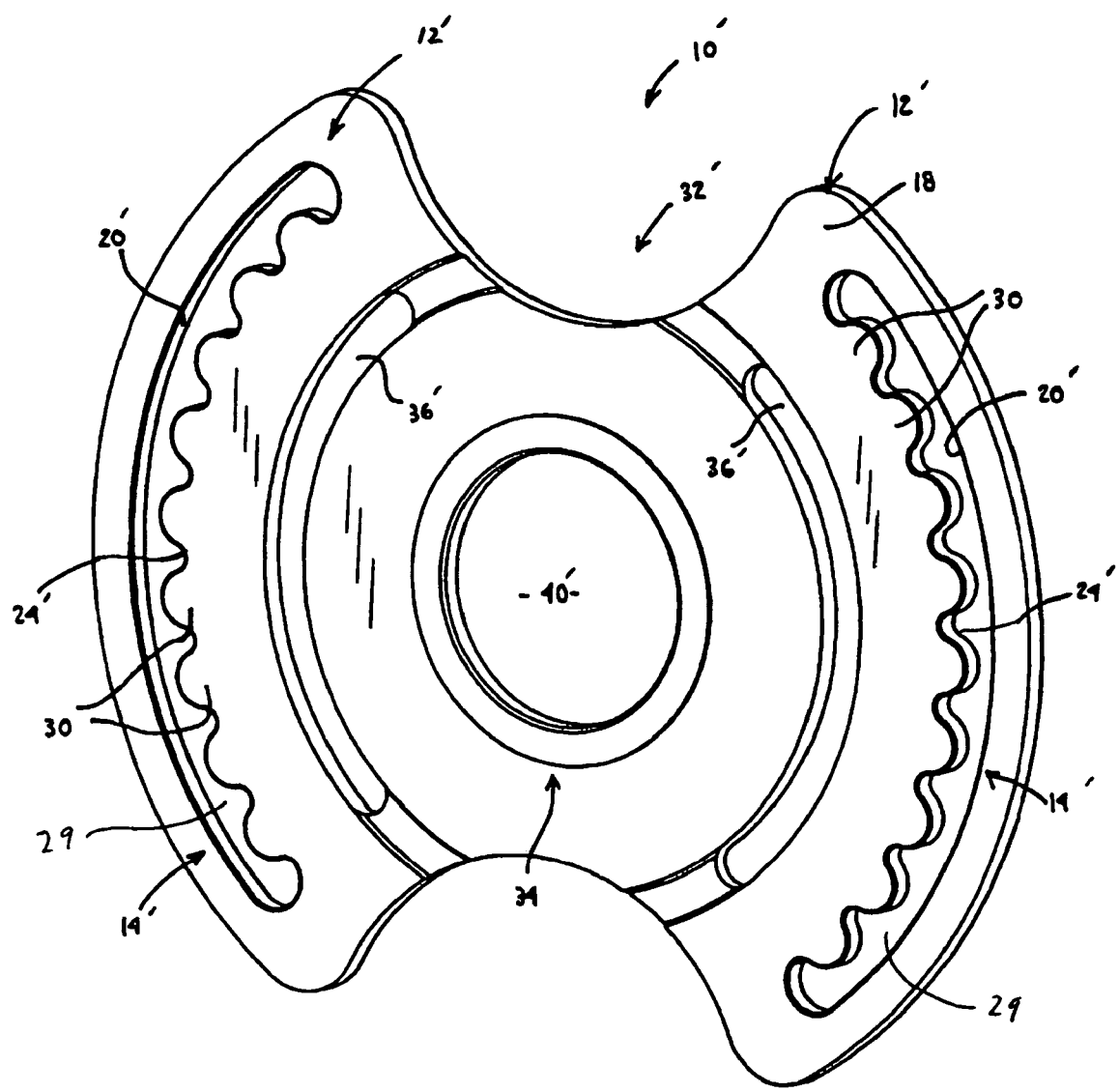
FIG. 7 is a perspective view of a second embodiment of a mounting member according to the principles of the present invention.
Figure 8:
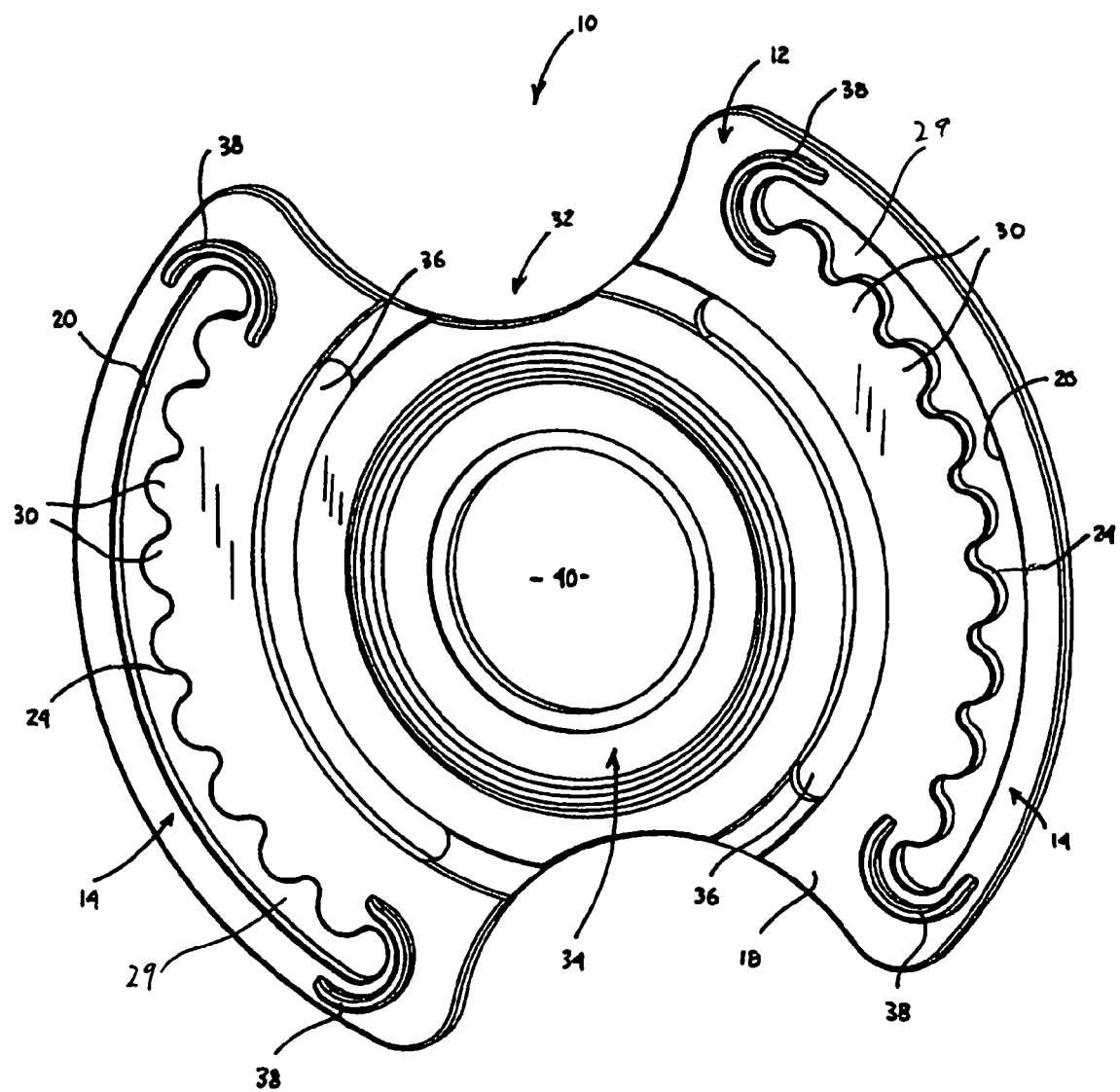
FIG. 8 is a perspective view of a third embodiment of a mounting member according to the principles of the present invention.
Figure 9:
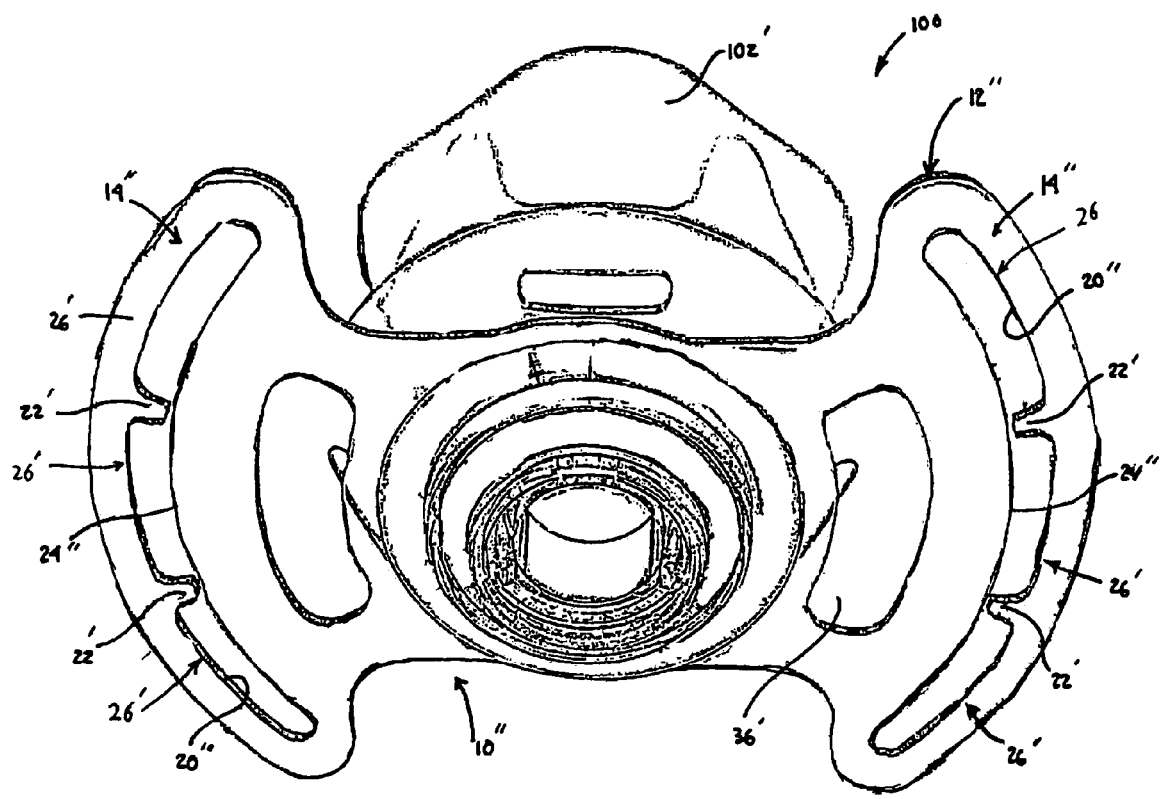
FIG. 9 is a perspective view of a patient interface device including a forth embodiment of a mounting member according to the principles of the present invention.

Turning to the embodiments of FIGS. 7 and 8, a single or multiple slots 29 may also include a tooth projection 30. As with ridges 22 of the previous embodiment, tooth projections 30 of the present embodiment also extend from an edge 24' of slot 29. However, in this embodiment, tooth projection 30 is urged against the strap (not shown), which is, in turn, urged against an opposing edge 20' of slot 29 acting as the above-discussed bearing surface 20. Such an arrangement helps in retaining the straps in strap attachment assembly 14 of mounting member 10. Further, this helps to ensure that the headgear assembly continues to maintain the requisite seal between the mask and the user's face A.

Referring again to FIGS. 2-6, in one embodiment, mounting member 10 is substantially in the form of a circular disk 32. Accordingly, a central portion 34 of the circular disk is rotatably attached to the mask in a position that is substantially adjacent mask port 106, which lies centrally on the mask. In this manner, circular disk 32 is fully rotatable 360° about the mask port.

As seen in various embodiments in the drawings, the present invention contemplates that mounting member 10 includes one or more flex slots 36. These flex slots 36 extend through and along a surface 18 of the disc and provide flexibility to the strap connection member 12 under torqued conditions. Depending upon the material of construction of the mounting member, the use of additional flex slots 36 provides a typically rigid or fairly inflexible material, such as plastic, with the ability to obtain higher flexibility characteristics and the ability to bend in certain situations.

Multiple flex slots 36 can be used, and each flex slot 36 extends through and along the mounting member. In one embodiment, and when using circular disk 32, flex slots 36 preferably extend through and along a portion of the strap connection member surface substantially adjacent to central portion 34 of the circular disk. Accordingly, the flex slots are positioned closer to the central portion 34 of the circular disk 32 than the slots 16. Of course, the present invention contemplates that the location of the flex slots on the mounting member, their size, and configuration can be selected to provide the desired flexibility of the mounting member.

Mounting member 10 may be formed from a variety of materials or combination of materials. For example, the mounting member can be formed from a substantially rigid material, or a substantially flexible material. For example, the mounting member can be formed from a plastic, a polymer, a rigid material, a flexible material, a molded material, a moldable material, a thermoplastic, etc. Still further, in one embodiment, and in order to provide additional structural integrity to the material of construction of the mounting member, various reinforced portions 38 may be provided. See FIGS. 3-6. These reinforced portions 38 are used to bolster the material of construction, such that the mounting member does not snap or break during torque conditions. In one embodiment, the mounting member is attached to mask 102 at a position substantially adjacent the mask port, and specifically against mask wall 108 adjacent mask port 106.

As discussed above, conduit coupling 112 can be provided for allowing fluid communication of gas into mask 102. In one embodiment, the conduit coupling includes a first end 116 and a second end 118. Mounting member 10 of this embodiment includes a coupling orifice 40 extending through the mounting member. When using the circular disk embodiment of the mask mounting mechanism, the coupling orifice extends through central portion 34 of the circular disk. In any case, first end 116 of the conduit coupling 112 extends through coupling orifice 40, and is therefore in fluid communication with the mask port and the mask.

Figure 13:
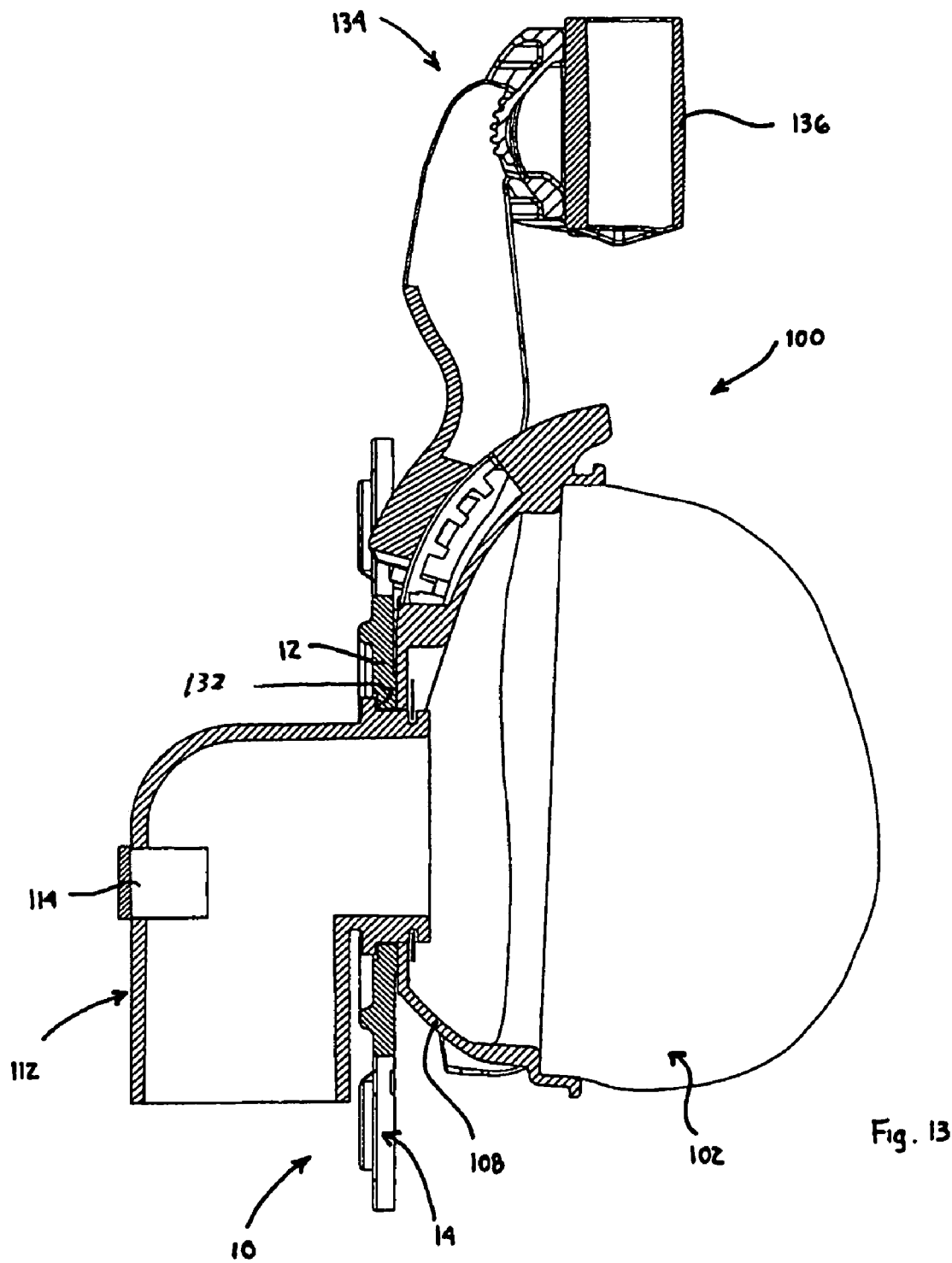
FIG. 13 is a side sectional view of a patient interface device.

In order to achieve proper attachment in this embodiment, the first end of the conduit coupling 112 includes a rim portion 120 and an extension portion 122. The rim portion is sized and shaped so as to retain mounting member 10, and the extension portion is sized and shaped so as to extend through and engage mask port 106. In this manner, the mounting member is retained between rim portion 120 of conduit coupling 112 and an outer surface 124 of mask wall 108. However, the mounting member, while retained in operative engagement with the mask, is continuously rotatable with respect to the mask. Accordingly, while the mounting member is "sandwiched" between conduit coupling 112 and mask 102, it still provides fully rotatable movement. In particular, as seen in FIG. 13, mounting member 10 is held between conduit coupling 112 and mask wall 108, and, in particular, between a rim 132 of conduit coupling 112 and mask wall 108. However, the mounting member is sized so as to allow rotation thereof between the rim and the wall.

Figure 10:
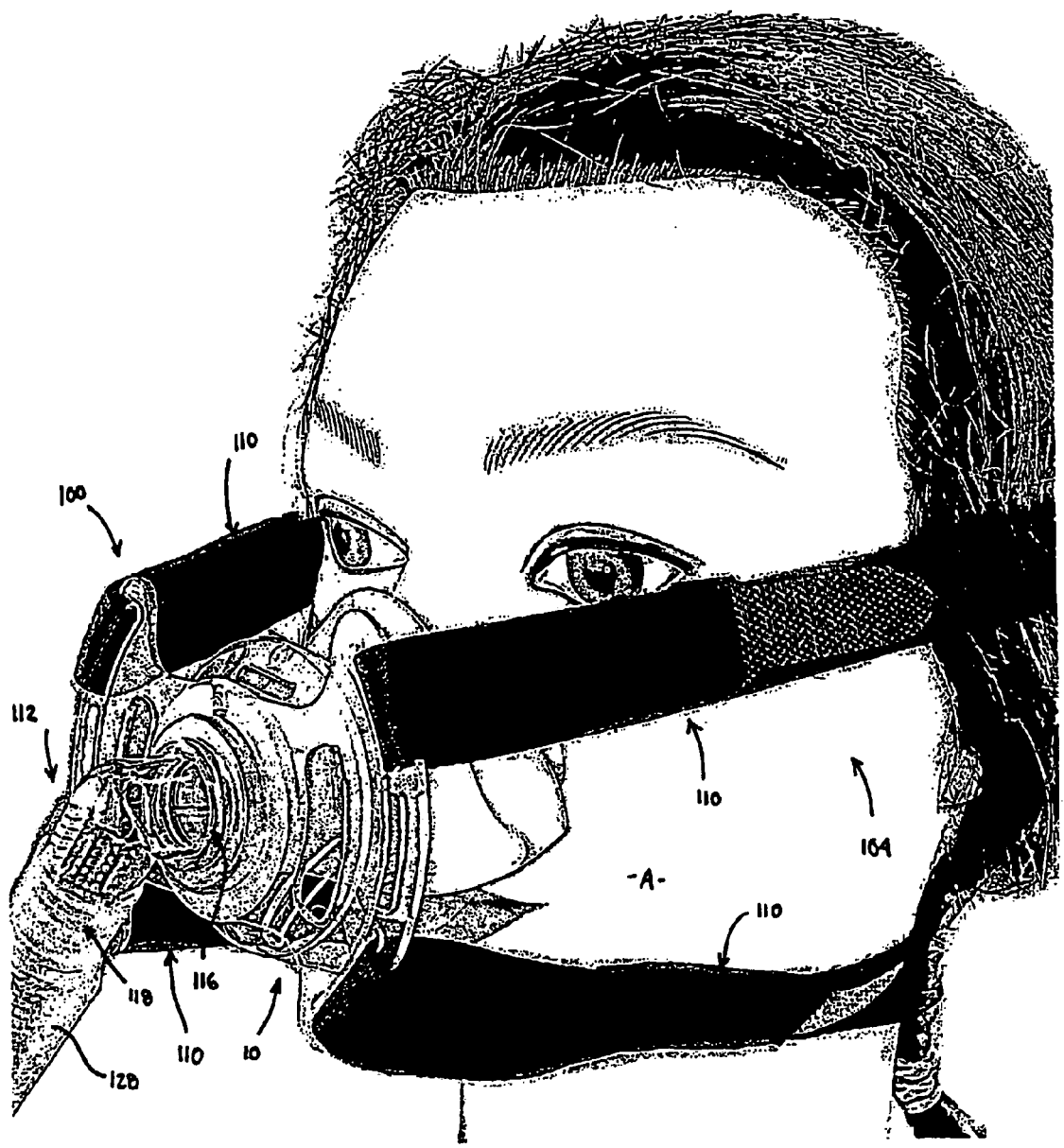
FIG. 10 is a perspective view of the patient interface device of FIG. 9 shown worn on a patient in a horizontal four-point mask attachment configuration.
Figure 11:
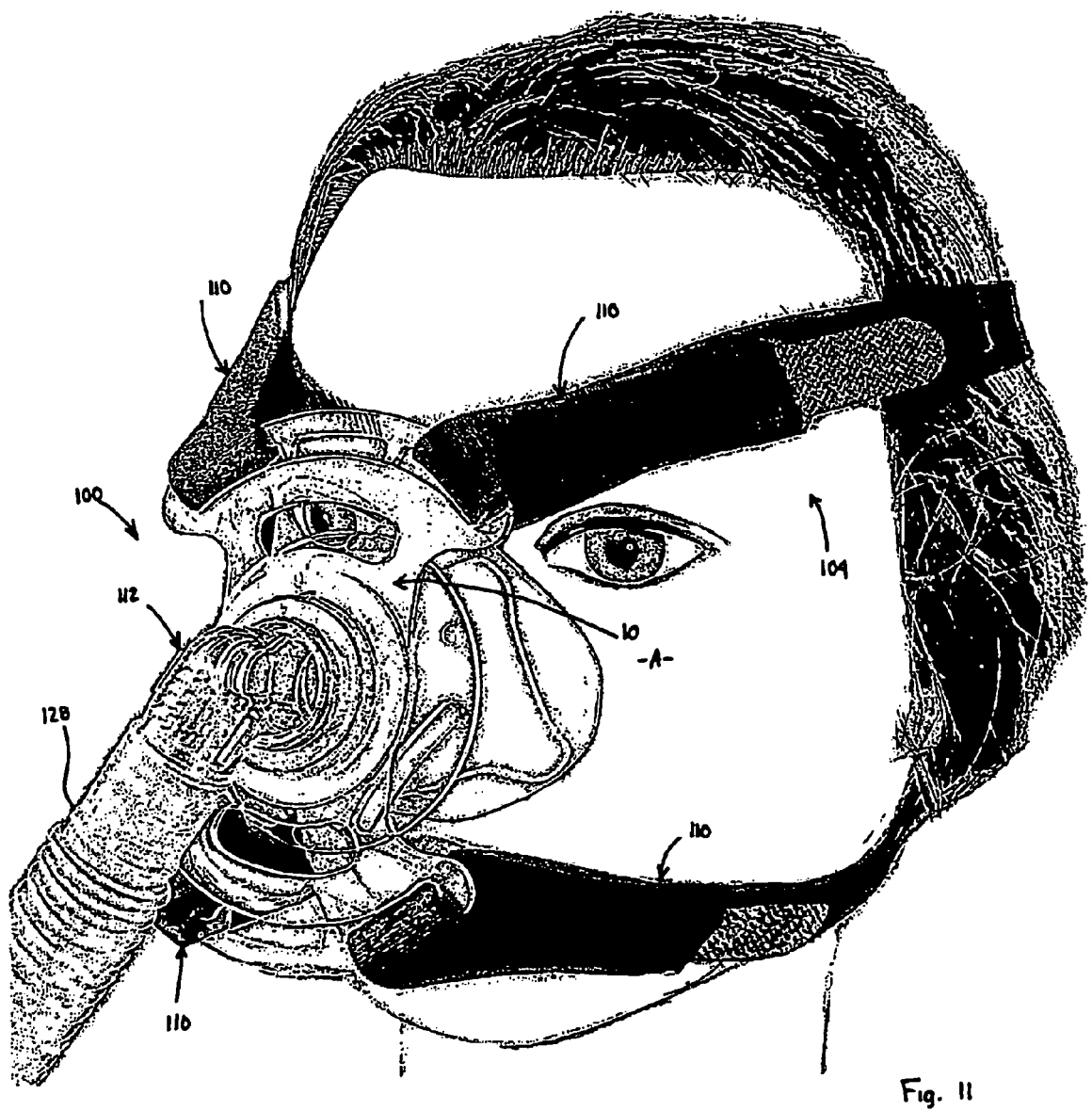
FIG. 11 is a perspective view of the patient interface device of FIG. 9 shown worn on a patient in a vertical four-point mask attachment configuration.
Figure 12:
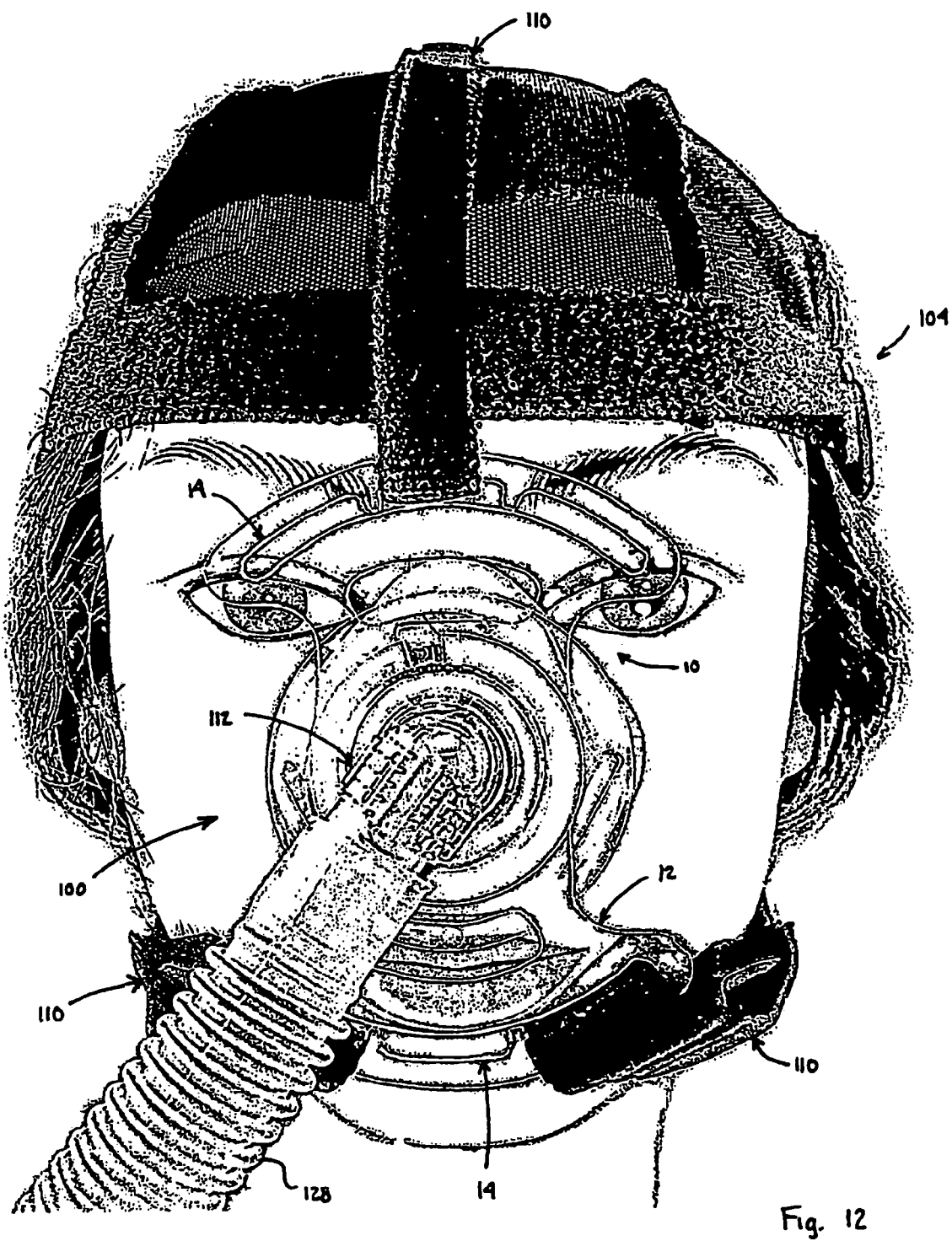
FIG. 12 is a perspective view of the patient interface device of FIG. 9 shown worn on a patient in a vertical three-point mask attachment configuration.

Mounting member 10 is useful in connection with a variety of headgear assemblies 104. For example, a user may select whether to use a three-point headgear assembly (FIG. 12), a four-point headgear assembly (FIGS. 10 and 11), a vertical headgear assembly (FIG. 12) and/or a horizontal headgear assembly (FIGS. 10 and 11). Regardless of which headgear assembly 104 is used, one or more of the attachment points is at the strap attachment assembly 14 of the strap connection portion 12 of the mounting member.

Further, as discussed above, the straps of the headgear assembly may be attachable and/or adjustable between varying positions of the strap attachment assembly 14. For example, the user may select from any one or more of the five recesses 26 in each slot 16 in the embodiment of FIGS. 3-6, anywhere along the bearing surface 20 of the slots 16 of the embodiment of FIGS. 7 and 8, or any one or more of the three recesses 26 of the embodiment of FIGS. 9-12. It is not only the multiple positions and bearing surfaces 20 that provide the adjustability and flexibility of mounting member 10 of the present invention, but also the rotatability of the mounting member, which allows the user to obtain and retain any fit of the headgear assembly that is desired.

While only the slot 16 for the strap attachment assembly 14 is discussed herein, any number of or different varieties of strap attachment assemblies are envisioned. For example, the present invention contemplates using a ball-and-socket arrangement, which provides additional rotatability and movement at the connection point, for the strap attachment assembly. Such a ball-and-socket arrangement is shown and described in published U.S. patent application Ser. No. 10/629,366 (Publication No. US-2004-0025883-A1) and PCT patent application No. PCT/US2003/024030 (PCT publication No. WO 2004/014454) to Eaton et al. The straps of the headgear assembly can be adjusted by the user or patient, and as already discussed, using the strap attachment assembly 14, such as the slot 16 arrangement, the ball-and-socket arrangement, etc., the straps can be removed from mounting member 10.

In a further embodiment, the patient interface device 100 includes a forehead support assembly 134 having a forehead contact member 136 for contacting a portion of a user's forehead. See FIG. 13. An example of one type of forehead support assembly is shown and described in published U.S. patent application Ser. No. 10/654,379 (Publication No. US-2004-0045551-A1) and PCT patent application No. (PCT publication No. WO 2004/021960) to Eaton. Further, such a forehead support assembly may include a padded element, such as a gel-filled pouch, or detachable gel-filled pouch, an example of which is shown and described in U.S. Pat. No. 6,467,483.

Figure 2:
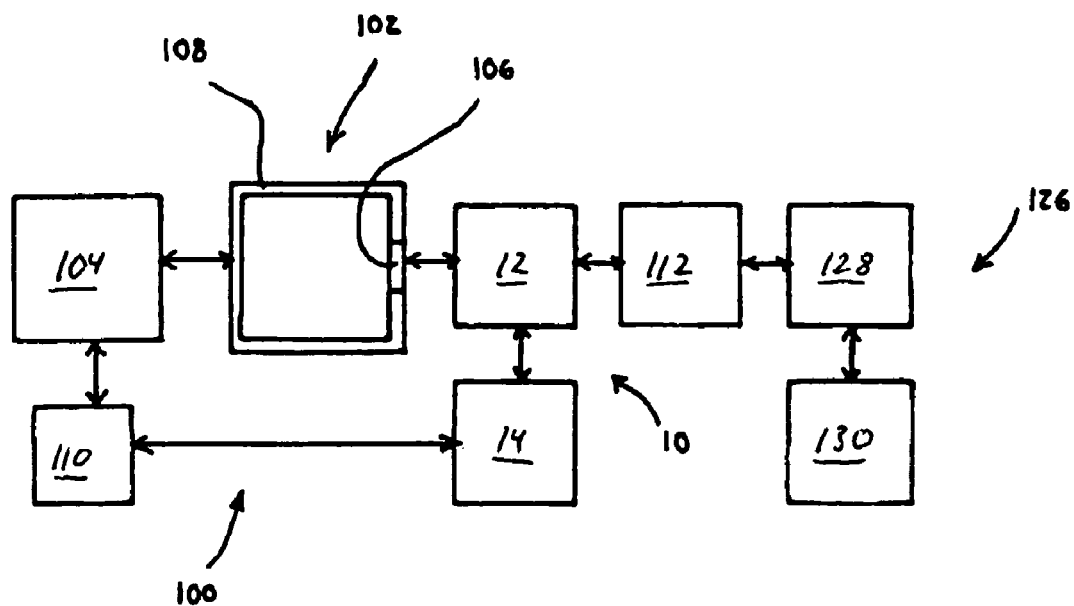
FIG. 2 is a schematic view of a patient interface device connected to a pressure support system, which includes a pressure support device and a patient circuit.
Figure 3:
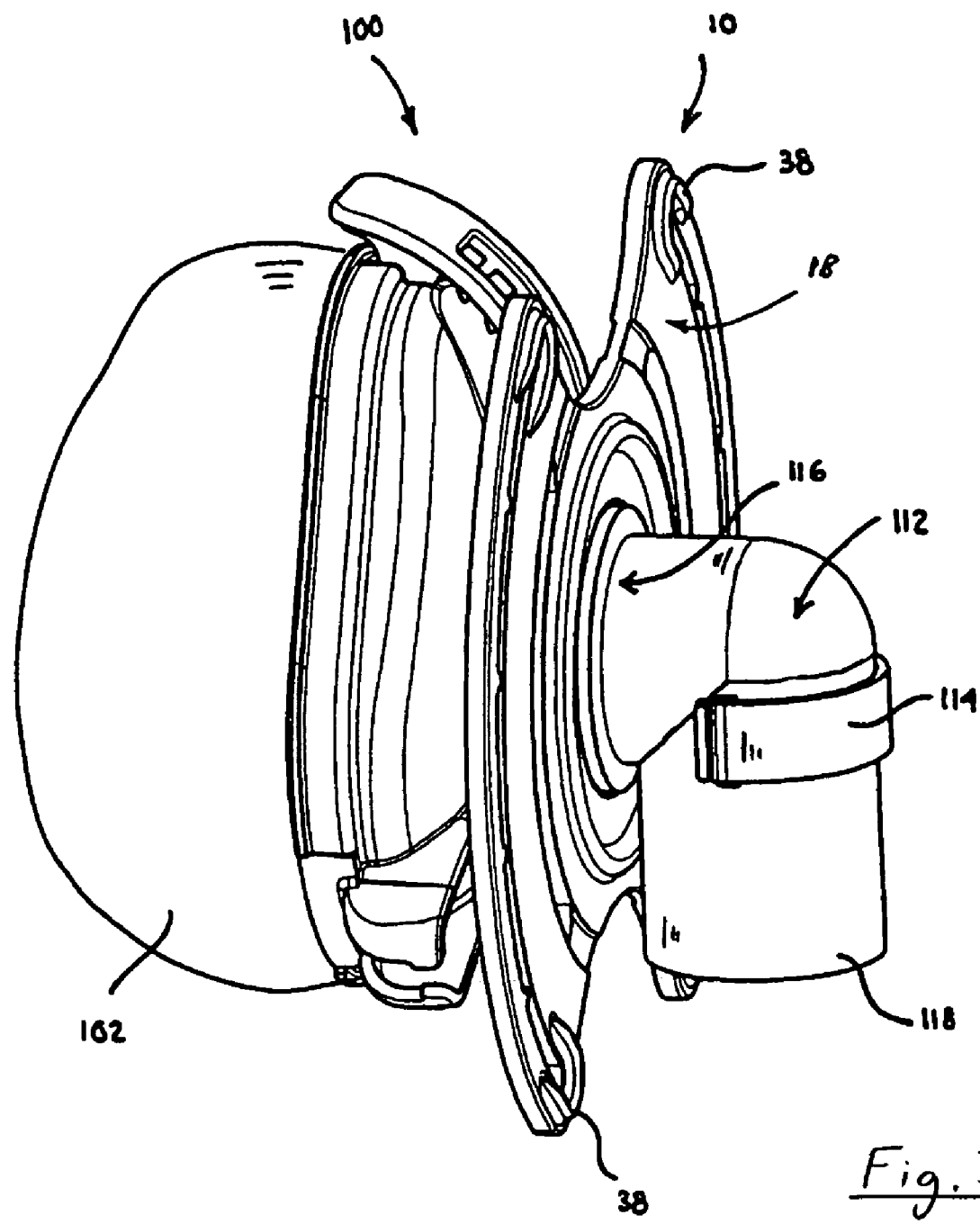
FIG. 3 is a perspective view of a patient interface device according to the principles of the present invention.
Figure 4:
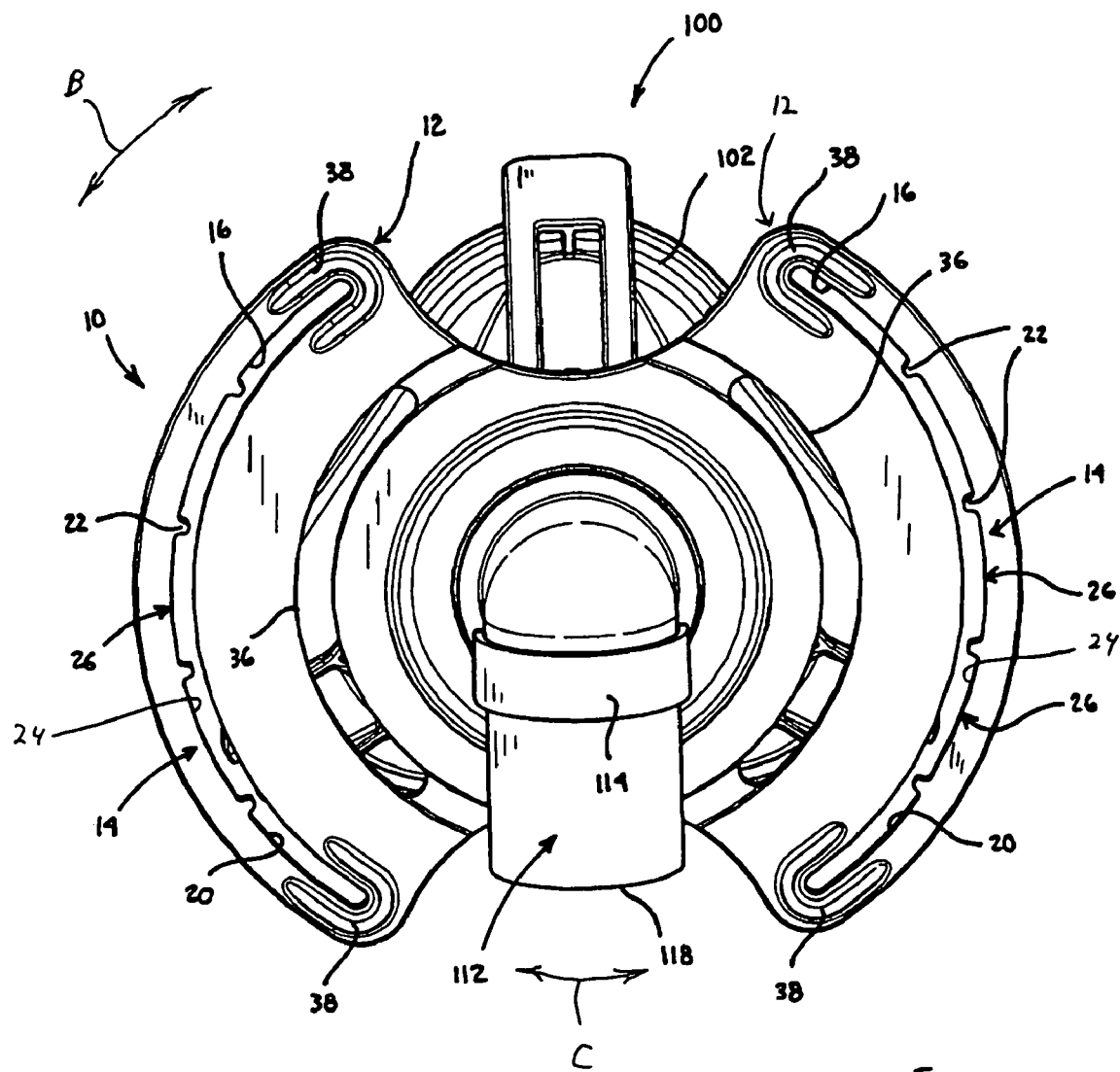
FIG. 4 is a front view of the patient interface device of FIG. 1.
Figure 5:
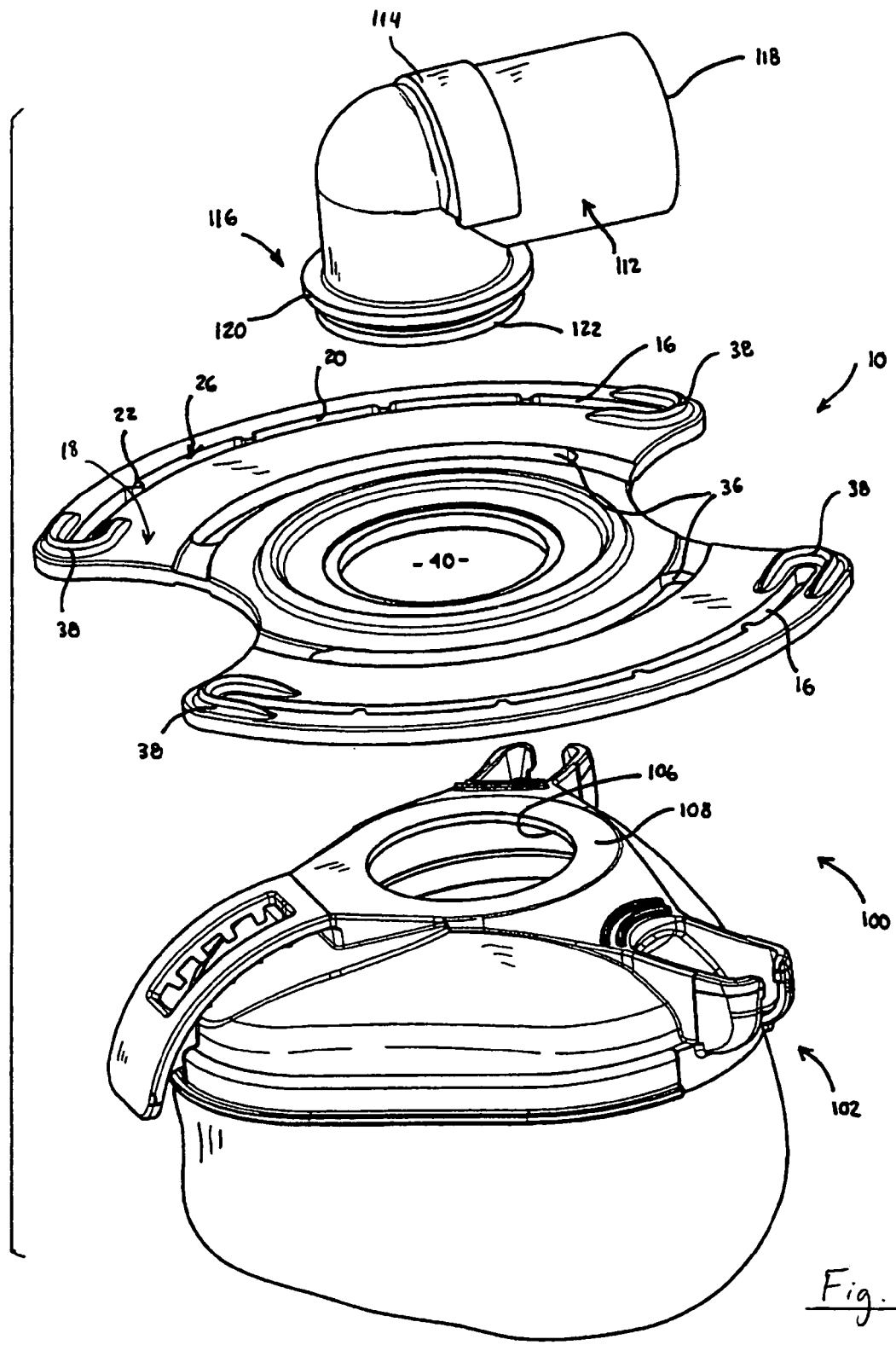
FIG. 5 is an exploded view of the mask patient interface device of FIG. 1.
Figure 6:
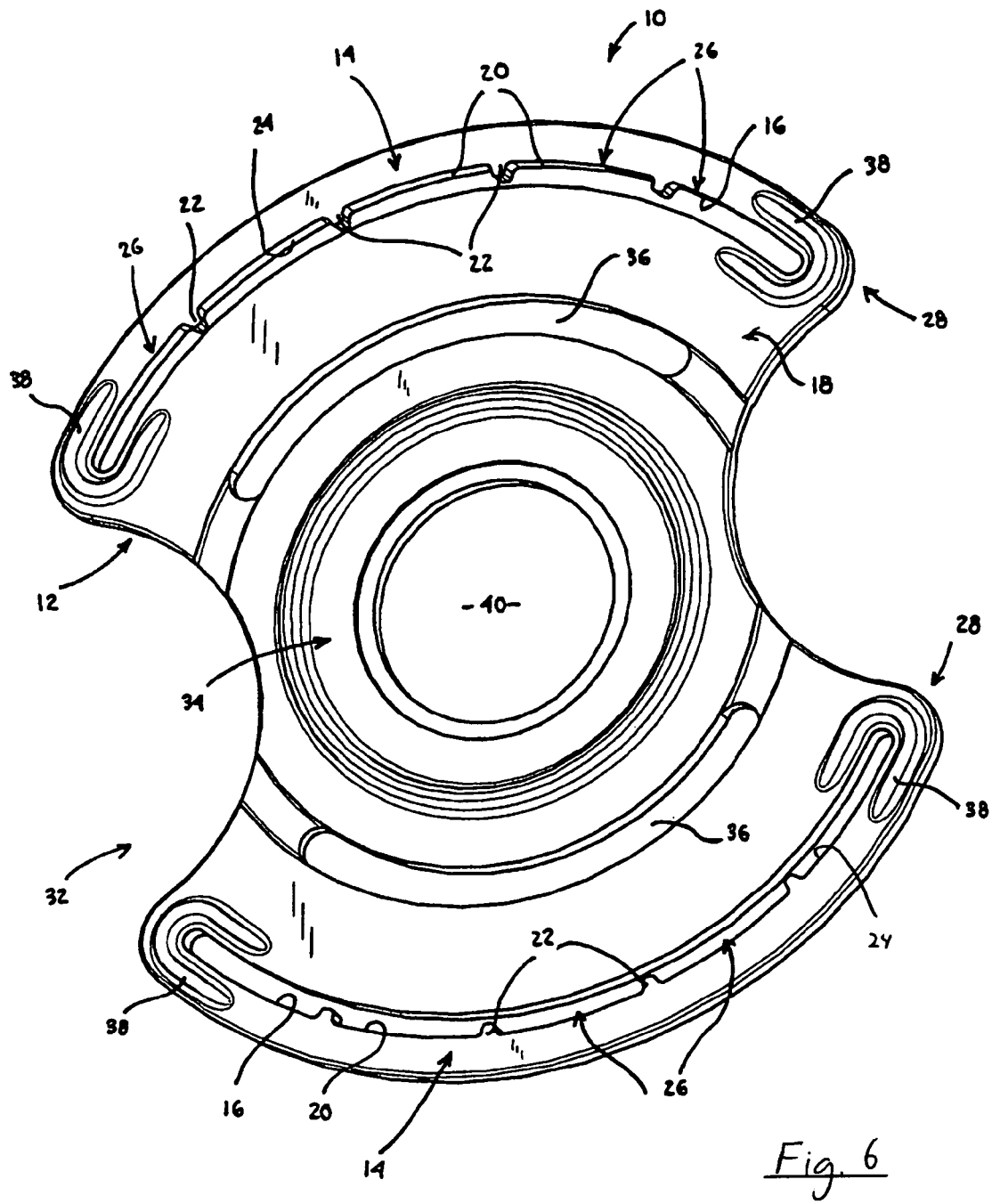
FIG. 6 is a perspective view of the mounting member for use in the patient interface device of FIG. 1.

In a still further embodiment, patient interface device 100 includes the conduit coupling 112, having first end 116 and second end 118. However, in this embodiment, the second end of the conduit coupling 112 is in fluid communication with a patient circuit 126. As seen in FIG. 2, this patient circuit may include a conduit 128 and a pressure support device 130. Patient circuit 126 is an arrangement that is known in the art. The patient circuit typically includes conduit 128 in fluid communication with pressure support device 130. In operation, the gas, typically oxygen or air, flows from the pressure support device, which may receive oxygen through an oxygen tank or other similar gas source, through the conduit, further through the conduit coupling 112 and mask port 106 and into mask 102, as discussed above. In this manner, the patient receives gas delivery for inhalation.

As seen in operation in FIGS. 1 and 10-12, the present invention provides a mounting member 10 in a patient interface device 100 that provides full rotatability and adjustability of the headgear assembly 104, such as a headgear with straps 110, with respect to mask 102. Any headgear assembly 104 is envisioned and usable in connection with the presently-invented mounting member 10, such as a headgear apparatus, as is known in the art. Further, the mounting member of the present invention provides flexibility of adjustment and movement without jeopardizing the seal between the mask 102 and the user's face A. The mounting member allows a patient wearing the mask much more flexibility of movement, such as when he or she is sleeping or exercising. In addition, mounting member 10 is fully rotatable with respect to the mask, such that a variety of pre-existing headgear assemblies, including headgear and different strap configurations, can be used in connection with mounting member 10. Still further, the mounting member is capable of being retrofitted on a variety of presently-existing and prior art masks and headgear assemblies.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device comprising:
   a shell having a wall with a port extending therethrough;
   a conduit coupling in fluid communication with the port; and
   a mounting member, including a strap connection portion, wherein the mounting member is rotatably coupled to the shell such that the mounting member is rotatable over a 360 degree range while the patient interface device is donned on a user and without locking in a fixed position relative to the shell while the patient interface device is donned on a user, wherein the port defines a rotation axis for the mounting member such that the mounting member rotates around the port, wherein the strap connection portion comprises a slot defined in the mounting member and adapted to be coupled to a strap of a headgear assembly, wherein the slot includes at least one ridge extending from an edge of the slot such that the slot is separated into a plurality of discrete recesses, and wherein each of the plurality of recesses is sized and configured to retain a strap of a headgear assembly.

2. The patient interface device of claim 1, further comprising a headgear assembly having at least one strap operatively coupled to the strap connection portion.

3. The patient interface device of claim 2, wherein the headgear assembly is a three-point headgear assembly, a four-point headgear assembly, a vertical headgear assembly, a horizontal headgear assembly, or a combination thereof.

4. The patient interface device of claim 1, wherein the conduit coupling has a first end operatively coupled to the shell and a second end adapted to be coupled to a patient circuit.

5. The patient interface device of claim 1, wherein the slot includes at least one tooth projection extending from an edge of the slot such that the tooth is urged against a strap of a headgear assembly and the strap is urged against an opposing edge of the slot, thereby acting as a bearing surface.

6. The patient interface device of claim 1, wherein the strap connection portion comprises a plurality of slots defined in a periphery of the mounting member.

7. A patient interface device comprising:
   a shell having a wall with a port extending therethrough;
   a conduit coupling in fluid communication with the port;
   a mounting member, including a strap connection portion, wherein the mounting member is rotatably coupled to the shell such that the mounting member is rotatable over a 360 degree range while the patient interface device is donned on a user and without locking in a fixed position relative to the shell while the patient interface device is donned on a user, wherein the port defines a rotation axis for the mounting member such that the mounting member rotates around the port, and wherein the mounting member is a generally circular disk, and wherein a central portion of the disk is rotatably attached to the shell in a position substantially adjacent the port.

8. A patient interface device comprising:
   a shell having a wall with a port extending therethrough;
   a conduit coupling in fluid communication with the port;
   a mounting member, including a strap connection portion, wherein the mounting member is rotatably coupled to the shell such that the mounting member is rotatable over a 360 degree range while the patient interface device is donned on a user and without locking in a fixed position relative to the shell while the patient interface device is donned on a user, and wherein the port defines a rotation axis for the mounting member such that the mounting member rotates around the port; and at least one flex slot defined in the mounting member to enhance a flexibility of the mounting member.

9. The patient interface device of claim 1, wherein the mounting member is formed from a substantially rigid material, a substantially flexible material, or a combination thereof.

10. A patient interface device comprising:
sealing means for contacting a surface of a user;
conduit coupling means for coupling the sealing means with a patient circuit such that a flow of gas is communicated between the sealing means and the patient circuit; and
mounting means, operatively coupled to the sealing means, the conduit coupling means, or both, for coupling the patient interface device to a headgear such that the mounting means is rotatably coupled to the sealing means, wherein the mounting means is rotatable over a 360 degree range while the patient interface device is donned on a user and without locking the mounting means in a fixed position relative to the sealing means, wherein a port in the sealing means defines a rotation axis for the mounting means such that the mounting means rotates around the port, and wherein the mounting means includes a strap connection portion comprising a slot defined in the mounting member and adapted to be coupled to a strap of a headgear assembly, wherein the slot includes at least one ridge extending from an edge of the slot such that the slot is separated into a plurality of discrete recesses, and wherein each of the plurality of recesses is sized and configured to retain a strap of a headgear assembly.

11. The patient interface device of claim 10, further comprising a headgear assembly having at least one strap operatively coupled to the strap connection portion.

12. The patient interface device of claim 11, wherein the headgear assembly is a three-point headgear assembly, a four-point headgear assembly, a vertical headgear assembly, a horizontal headgear assembly, or a combination thereof.

13. A patient interface device comprising:
a shell having a wall with a port extending therethrough;
a conduit coupling in fluid communication with the port; and
a mounting member, including a strap connection portion, wherein the mounting member is rotatably coupled to the shell such that the mounting member is rotatable over a 360 degree range while the patient interface device is donned on a user and without locking in a fixed position relative to the shell while the patient interface device is donned on a user, wherein the port defines a rotation axis for the mounting member such that the mounting member rotates around the port, wherein the strap connection portion comprises a slot defined in the mounting member and adapted to be coupled to a strap of a headgear assembly, and wherein the slot includes at least one tooth projection extending from an edge of the slot such that the tooth is urged against a strap of a headgear assembly and the strap is urged against an opposing edge of the slot, thereby acting as a bearing surface.

14. The patient interface device of claim 13, further comprising a headgear assembly having at least one strap operatively coupled to the strap connection portion.

15. The patient interface device of claim 13, wherein the mounting member is formed from a substantially rigid material, a substantially flexible material, or a combination thereof.

16. A patient interface device comprising:
sealing means for contacting a surface of a user;
conduit coupling means for coupling the sealing means with a patient circuit such that a flow of gas is communicated between the sealing means and the patient circuit; and
mounting means, operatively coupled to the sealing means, the conduit coupling means, or both, for coupling the patient interface device to a headgear such that the mounting means is rotatably coupled to the sealing means, wherein the mounting means is rotatable over a 360 degree range while the patient interface device is donned on a user and without locking the mounting means in a fixed position relative to the sealing means, wherein a port in the sealing means defines a rotation axis for the mounting means such that the mounting means rotates around the port, and wherein the mounting means includes a strap connection portion comprising a slot defined in the mounting member and adapted to be coupled to a strap of a headgear assembly, and wherein the slot includes at least one tooth projection extending from an edge of the slot such that the tooth is urged against a strap of a headgear assembly and the strap is urged against an opposing edge of the slot, thereby acting as a bearing surface.

17. The patient interface device of claim 16, further comprising a headgear assembly having at least one strap operatively coupled to the strap connection portion.

18. The patient interface device of claim 16, wherein the mounting member is formed from a substantially rigid material, a substantially flexible material, or a combination thereof.

19. A patient interface device comprising:
a shell having a wall with a port extending therethrough;
a conduit coupling in fluid communication with the port; and
a mounting member, including a strap connection portion, wherein the mounting member is rotatably coupled to the shell such that the mounting member is rotatable over a 360 degree range while the patient interface device is donned on a user and without locking in a fixed position relative to the shell while the patient interface device is donned on a user, wherein the port defines a rotation axis for the mounting member such that the mounting member rotates around the port, and wherein the mounting member is defined by a substantially rigid material such that the mounting member does not substantially deflect response to a force being appled to the strap connection portion.

20. The patient interface device of claim 19, further comprising a headgear assembly having at least one strap operatively coupled to the strap connection portion.

* * * * *